United States Patent [19]

Mattes

[11] Patent Number: 5,759,514
[45] Date of Patent: Jun. 2, 1998

[54] COMPOSITION FOR DELIVERY OF TOXIC RADIOISOTOPES TO THE CELL NUCLEUS AND USE

[75] Inventor: M. Jules Mattes, Berkeley Heights, N.J.

[73] Assignee: Center For Molecular Medicine and Immunology, Newark, N.J.

[21] Appl. No.: 695,182

[22] Filed: Aug. 1, 1996

Related U.S. Application Data

[63] Continuation of Ser. No. 235,319, Apr. 29, 1994, abandoned.

[51] Int. Cl.$^6$ .................... A61K 51/00; A61M 36/14
[52] U.S. Cl. .................... 424/1.65; 424/1.11; 424/1.73
[58] Field of Search .................... 424/1.49, 1.53, 424/1.65, 1.85, 1.11, 1.73, 1.81; 530/391.5

[56] References Cited

U.S. PATENT DOCUMENTS

| | | | |
|---|---|---|---|
| 4,547,569 | 10/1985 | Letsinger et al. | 536/29 |
| 4,671,958 | 6/1987 | Rodwell et al. | 424/85 |
| 4,757,072 | 7/1988 | Kabbe et al. | 514/257 |
| 4,894,348 | 1/1990 | Ronald et al. | 436/546 |
| 5,057,313 | 10/1991 | Shih et al. | 424/85.91 |
| 5,059,413 | 10/1991 | Reardan et al. | 424/4.1 |
| 5,096,694 | 3/1992 | Quivy et al. | 424/1.1 |
| 5,130,116 | 7/1992 | Woo et al. | 424/1.1 |
| 5,175,273 | 12/1992 | Bischofberger et al. | 536/27 |
| 5,332,567 | 7/1994 | Goldenberg | 424/1.49 |

FOREIGN PATENT DOCUMENTS

WO 90/03799  4/1990  WIPO .

OTHER PUBLICATIONS

Pittman et al., *Biochem. Journal*, vol. 212, pp. 791–800, 1983.

Shih, Lisa B. et al., "The Processing and Fate of Antibodies and Their Radiolabels Bound to the Surface of Tumor Cells in Vitro: A Comparison of Nine Radiolabels", *The Journal of Nuclear Medicine*, vol. 35, No. 5, pp. 899–908 (May 1994).

Kyriakos, Raymond J. et al., "The Fate of Antibodies Bound to the Surface of Tumor Cells in Vitro", *Cancer Research*, 32, pp. 835–842 (Feb. 1992).

Cowan, D.S.M. et al., "Targeting Radiosensitizers to DNA by Attachment of an Intercalating Group: Nitroimidazole–Linked Phenanthridines", *Radiation Research*, 127, pp. 81–89 (1991).

Kinsey, Berma M. et al., "Synthesis and Biological Activity of the Intercalating Agent 3-Acetamido-5-[$^{123/125}$I] iodo–6–aminoacridine", *Nucl. Med. Biol.*, vol. 17, No. 3, pp. 341–346 (1990).

Roberts, Peter B. et al., "Hypoxia–selective radiosensitization of mammalian cells by nitracrine, an electron–affinic DNA Intercalator", *Int. J. Radiat. Biol.*, vol. 51, No. 4, pp. 641–654 (1987).

Martin, Roger F. et al., "Cytotoxicity of an $^{125}$I–labled DNA–binding Compound That Induces Double–Stranded DNA Breaks", *Cancer Research*, 39, pp. 3244–3247 (Aug. 1979).

Adams, Adrienne et al., "Interaction of DNA–Intercalating Antitumor Agents with Adrenoceptors", *Molecular Pharmacology*, 27, pp. 480–491 (1985).

Warters, R.L. et al., "Radionuclide Toxicity in Cultured Mammalian Cells: Elucidation of the Primary Site of Radiation Damage", *Current Topics in Radiation Research Quarterly*, 12, pp. 389–407 (1977).

Martin, Roger F., "Induction of double-stranded breaks in DNA by binding with an $^{125}$I–labelled acridine", *Int. J. Radiat. Biol.*, vol. 32, No. 5, pp. 491–497 (1977).

*Primary Examiner*—John Kight
*Assistant Examiner*—Dameron Jones
*Attorney, Agent, or Firm*—Foley & Lardner

[57] ABSTRACT

A conjugate of a tumor cell-targeting protein or polypeptide and a nucleic acid-targeting small molecule labeled with an Auger electron-emitting radionuclide is useful for tumor therapy. The tumor cell-targeting protein or polypeptide may be an antibody or fragment thereof, a hormone or a growth factor.

4 Claims, No Drawings

COMPOSITION FOR DELIVERY OF TOXIC RADIOISOTOPES TO THE CELL NUCLEUS AND USE

This is a continuation of 08/235,319, filed Apr. 29, 1994.

BACKGROUND OF THE INVENTION

The field of the invention is anti-tumor chemotherapy. More particularly, the invention relates to the delivery of cytotoxic radioisotopes to the nucleus of a tumor cell using a targeting protein or polypeptide conjugated with a radiolabeled nucleic acid-targeting small molecule.

Certain radioisotopes, particularly Auger electron emitting radioisotopes such as 123I and 125I, are known to be very toxic to viable cells, but only if they are localized within the nucleus of the cell (Warters et al., *Curr. Top. Rad. Res.*, 12: 389 (1977)). Antibodies with some selectivity for tumor cells, relative to normal cells, are known, but antibodies themselves are unable to efficiently reach the nucleus. Most such antibodies react with the cell surface, and are gradually internalized, routed to lysosomes, and degraded (Kyriakos et al., *Cancer Res.*, 52: 835 (1992)). Degradation products, including any radioisotopes attached thereto, then gradually leave the cell by crossing the lysosomal membrane and then the cell membrane. Although a conventional radioisotope label on an antibody degradation product can theoretically pass through the nuclear membrane and deliver some radioactivity to the nucleus (Woo et al., WO90/03799), actual observations show that the amount is very slight—insufficient to lead to cytotoxicity of the tumor cell. The prior art indicates that conventional iodine is rapidly released from the cell after antibody catabolism.

Protein and polypeptide hormones and growth factors, particularly those with cell surface receptors, may be directly radiolabeled and used to target a tumor cell. However, as with the use of targeting antibodies directly radiolabeled, radioisotopes bound to amino acid residues of hormones and growth factors exit from the cell after catabolism, and do not bind to nuclear nucleic acid.

An important need persists for a composition capable of targeting a tumor cell and being endocytosed and degraded by such cell, and capable of delivering to the nucleus a radioisotope capable of interacting with nuclear material and thereby being cytotoxic. Such an invention is described below.

SUMMARY OF THE INVENTION

It is an object of the invention to provide a covalent conjugate between a tumor-targeting protein or polypeptide and a radiolabeled nucleic acid-targeting small molecule, the small molecule, after being liberated lytically from the targeting protein by an intracellular enzyme endogenous to the targeted tumor cell, being capable of passing through the lysosomal and nuclear membranes and intercalating a nuclear component, whereby the decay of the small molecule-bound radioisotope that emits cytotoxic Auger electrons destroys the nuclear component and consequently the viability of the targeted tumor cell.

It is also an object of the invention to provide methods of producing the aforementioned conjugate.

It is still another object of the invention to provide a method of treating a tumor comprising administering to a tumor-bearing subject a composition comprising a tumor cell targeting conjugate as described above.

A therapeutic anti-tumor conjugate comprising a tumor cell-targeting protein or polypeptide covalently conjugated to a nucleic acid-targeting small molecule derivatized with an Auger electron-emitting radioisotope, wherein said conjugate is capable of accreting at the surface of the tumor cell and being endocytosed into the tumor cell, wherein the endocytosed conjugate is capable of being lytically decomposed to products including the radiolabeled small molecule, wherein the liberated radiolabeled small molecule enters the nucleus of the tumor cell and binding to a nucleic acid present therein, said binding including intercalation into DNA, and wherein the radiolabel is capable of decomposing the nucleic acid to which the small molecule is bound thereby being cytotoxic to the tumor cell.

A method of treating a patient having a tumor comprising the step of administering to the patient the aforementioned therapeutic anti-tumor conjugate in therapeutically effective amounts in a pharmaceutically acceptable vehicle.

These and other objects will become apparent by reference to the specification and the appended claims.

DETAILED DESCRIPTION OF THE PREFERRED EMBODIMENTS

The general form of this invention is a small molecule that intercalates with DNA or other nuclear nucleic acid material, that is covalently conjugated to a tumor cell targeting protein or polypeptide, and that is labeled with an Auger electron-emitting radioisotope that is toxic to cells if it decays within the nucleus.

A preferred form of the invention is a nucleic acid-binding or DNA-intercalating small molecule labeled with one or more of $I^{125}$, $I^{131}$ and $^{32}p$ or both, conjugated to a tumor-targetting antibody or fragment thereof. It is also preferred that the targeting protein or polypeptide be a hormone or growth factor. These radionuclides are readily available at high specific activity, can be used to label nucleic acid binding and DNA-intercalating small molecules, and are very toxic. The toxicity is due to the emitted Auger electrons. Auger electrons are also emitted by a large number of other radioisotopes, all of which fall within the scope of this invention, for example, $^{77}$Br, $^{225}$At, $^{213}$Bi, $^{111}$In, and 188Rh.

Many nucleic acid-binding and DNA-intercalating small molecules suitable in practising this invention can be radiolabeled by standard oxidative iodination, using chloramine T or Iodogen, and can then be conjugated to antibodies by any one of many standard procedures. The conjugation method must be efficient, in order to use the radioisotope efficiently. Such small molecules suitable in practicing this invention include, but are not limited to, fluorescein and derivatives thereof, acridine and derivatives thereof, diacridine and derivatives thereof, anthracyclines and bis-anthracyclines, diaminoacridines linked by a short alkyl chain, phenanthridines such as 2-nitroimidazole phenanthridine and bis-phenanthridines, aminoacridines such as 3-acetamido-5-iodo-6-aminoacridine, ethidium bromide derivatives, diquinolines, nitracrine, phenanthridium conjugated to an oligonucleotide recognition system by a linker, daunomycin, mepacrine, acridine orange, methidium spermine, pyrimidone nucleoside bases containing fused aromatic polycyclic rings, quinazoline derivatives such as the 8-amino-12-oxo-10,12-dihydroindolo derivative, Hoechst 33258 and fluorescent dyes.

Cell Lines, Antibodies, and Radiolabeling

Cell lines used to test the conjugates of the invention and monoclonal antibodies (mAbs) useful for making conjugates according to the invention are readily available (see, for example, Kyriakos et al., above; Mattes et al., *Cancer*

(Suppl.) 73: 787 (1994); Ong et al., *Molec. Immunol.* 30: 1455 (1993); Demignot et al, *Cancer Immunol. Immunotherap.* 33: 359 (1991); Ali et al., *Cancer Res.* 50: 783S (1990); Halpern et al., *Cancer Res.* 43: 5347 (1983); Anderson-Berg et al., *Cancer Res.* 47: 1905 (1987), all of which are incorporated herein by reference). mAbs used in the experiments can be mouse IgG antibodies, but humanized and human antibodies fall within the scope of this invention. MAb MA103 reacts with high avidity to a high density antigen present on all human tumor cell lines tested, and is processed similarly to most other antibodies reacting with the cell surface (Mattes et al., 1994, above)). The human carcinoma cell line ME180 may be obtained from the American Type Culture Collection (Rockville, Md.). Radiolabeled antibodies are routinely monitored by SDS-PAGE and autoradiography, as described previously (Cairncross et al., *Proc. Natl. Acad. Sci* USA, 79: 5641 (1982)), and at least 90% of the radiolabel was present in the IgG subunits. Conjugates should be tested for stability in tissue culture medium for at least 3 days, by precipitation at various times with TCA, as described below. Conventional direct labeling of antibodies with $^{125}I$ may be carried out as described previously (Kyriakos et al., above).

Conjugation of antibodies with $^{125}I$-fluorescein may be achieved conventionally. In one procedure, starting with radiolabeled fluorescein isothiocyanate (Sigma Chemicals, St. Louis, Mo.), 25 μl at 13 μg/ml in 0.05M TrisHCl, pH 8.0, is added to a 0.5 ml microfuge tube that has been precoated with Iodogen (Pierce), as described by Pittman et al. (*Biochem. J.*, 212: 791 (1983)). Two mCi (74 MBq) $^{125}I$ in the same buffer are added. After 30 min at room temperature, the solution is transferred to a another microfuge tube containing 0.1 mg IgG in 0.2 ml 0.1M sodium carbonate buffer, pH 9.5. After incubating overnight at 4° C., the conjugate is purified by gel filtration on a PD-10 column. The specific activity of the product is typically about 0.3 mCi/mg (11.1 MBq/mg).

Conjugation of antibodies with fluorescein-β-D-galactopyranoside (Sigma F-4146) may be achieved according to Strobel et al., (*Arch. Biochem. Biophys.*, 240: 635 (1985)) developed for other galactose-containing molecules. To Iodogen-coated microfuge tubes is added 25 μ0.5M $KPO_4$ buffer, pH 7.0, containing 1–10 nmole fluorescein-galactoside (the yield and final specific activity does not substantially vary over this concentration range). After adding 1–2 mCi (37–74 MBq) $^{125}I$ in 25 μl of the same buffer, samples are incubated 30 min at room temperature, then transferred to another microfuge tube containing 4 Units of galactose oxidase (Sigma G-3385) in 5 μl of the same buffer. After 45 min at 37° C., 0.1 mg IgG in 50 μl phosphate-buffered saline is added, followed immediately by 2.1 μl of 2.0M sodium cyanoborohydride. After 3 hr at 37° C., the conjugate is purified on a PD-10 column as described above. Incorporation of $^{125}I$ ranged from 9–11%, and the specific activity of the product ranged from 0.8–1.0 mCi/mg (30–37 MBq/mg). To ensure that labeling is in fact by the intended method, controls are performed in which galactose oxidase is omitted, which should result in no significant incorporation.

Iodination with DTAF may be carried essentially according to Rushfeldt et al., *Cancer Res.*, 53: 658 (1993), with quantities of the reagents greatly reduced. One nmole DTAF in 25 μl 0.1M sodium borate buffer, pH 9.0, is added to an Iodogen-coated tube. One mCi (37 MBq) $^{125}I$ is added in 25 μl, and incubated 30 min at room temperature. The reaction mixture is transferred to a tube containing 10 μl of $Na_2S_2O_3$ at 1.0 mg/ml. After 3 min at room temperature, 25 μg IgG is added in ≤50 μl phosphate-buffered saline, and incubated 2 hr at room temperature. After addition of glycine to a final concentration of 50 mM, followed by a 30 min incubation at 37° C., the sample may be purified as described above. The iodination efficiency is generally in the range of 8–10%, resulting in a specific activity of approximately 3–5 mCi/mg (111–185 MBq/mg).

Antibody Retention Experiments

As described previously in detail (Kyriakos et al. above), confluent cells in 96-well plates are incubated with $5 \times 10^5$ cpm antibody for 2 hr at 37° C., then washed 4 times. Two-tenths ml tissue culture medium is added, and incubation continued for various times, e.g., from 4 hr to 7 days. At various times, 0.1 ml of supernatant is collected (½ of the total supernatant), and, after further washing, the cells are solubilized with 2.0M NaOH. After determining the cpm in the supernatant, samples are precipitated with 5 ml cold 10% TCA, and the precipitate collected by centrifugation for 15 min at 6,000 rpm in a Sorvall SS-34 rotor. In control wells, which may be included in every experiment, a large excess of unlabeled antibody is added to some wells; the cpm binding under these conditions is considered to be nonspecific; in all experiments, at least 80–90% of activity bound is generally bound specifically. The specific activity of the different labels may vary over approximately a 7-fold range; however, we previously found that a similar variation in antibody concentration had no significant affect on antibody processing (Kyriakos et al., above), at least with a conventional $^{125}I$ label.

The binding of radiolabeled, nucleic acid-targeting small molecules to nuclear components may be determined after administration of the conjugates of the invention by lysing cells in the cold, isolating nuclei by conventional techniques of cell fractionation, and determining radioactivity in the nuclear fraction. By testing in parallel tumor cell viability after treatment with a conjugate according to the invention, a correlation may be made between the amount of radiolabel bound to nuclear components and the cytoxicity of the radiolabel.

Miscellaneous Methods

Galactosamine-conjugated bovine albumin may be purchased from Sigma Chemicals (#A-1159), and iodinated with chloramine T as described above. It may be used in binding and processing experiments just as described for iodinated antibodies, with galNAc-BSA used at 0.5 mg/ml in control wells to determine nonspecific binding.

Administration to Patients

The conjugates of the invention, dissolved or suspended in conventional pharmaceutically acceptable vehicles (see REMINGTON'S PHARMACEUTICAL SCIENCE), may be administered parenterally to a patient by conventional procedures. Dosages will be determined by factors including the patient's size and weight and other medical conditions, and by the stage of the tumor invasion. These determinations would not require undue experimentation by those skilled in the clinical arts.

The following examples are provided to describe embodiments of the invention and are not in any way to be construed as limiting the scope of the invention which is described in the specification and the appended claims.

EXAMPLE 1

Antibodies Labeled with Iodinated Fluorescein Derivatives

In preliminary experiments, to demonstrate the susceptibility of fluorescein to iodination, FITC-dextran (Sigma Chemicals, #FD-20s) was iodinated under the conditions normally used for iodinating proteins. Fifty µg FITC-dextran, with average molecular weight of 17,000, was iodinated with approximately the same efficiency, 30–40%, as generally obtained with the same weight of IgG . Iodofluorescein was conjugated to antibody MA103 using FITC, which was radiolabeled immediately before protein conjugation. This conjugation resulted in a relatively low specific activity, of approximately 0.5 mCi/mg (18.5 MBq/mg), but this was sufficient to determine the fate of the radiolabel after antibody binding to the cell surface. A second procedure for conjugation of iodofluorescein was developed using fluorescein-galactoside, following the method developed by Strobel et al. above. Following iodination, the galactose moiety was oxidized by galactose oxidase, then conjugated to amino groups on MA103 by reductive amination via a Schiff base. This conjugation method resulted in approximately 10% efficiency of iodination and a specific activity of approximately 1 mci/mg (37 MBq/mg). Incorporation of these radiolabels into the IgG subunits was demonstrated by SDS-PAGE (data not shown). In 2–3 experiments with these radiolabels, significant differences in processing between iodo-FITC or iodo-fluorescein-galactose and conventional iodine were not detected (Table 1).

to depend not on the mode of iodination, but rather on the carrier protein. Further investigation indicated, however, that the ligand was binding to the plastic wells, rather than to the cells. Evidence supporting this conclusion includes the following. 1) Trypsinization of the cells, as performed previously with the $^{111}$In label, did not result in the association of radioactivity with the cell pellet. Only 1–2% of the cpm were associated with the cells, and only 2% was present in the supernatant of the trypsinized, pelleted cells. In contrast, 89–91% of the cpm remained in the "empty" wells, and were extracted with 2.0M NaOH. Further experiments demonstrated that these plastic-bound counts were not extracted with 2% SDS. 2) Experiments performed with "empty" wells, that had no cells but had been preincubated with tissue culture medium, demonstrated very similar binding and "processing" as with wells containing cells. Therefore, the lack of catabolism of this ligand can be attributed to the fact that it is binding to the plastic rather than to the cells. Additional experiments demonstrated that binding of the ligand to plastic did not require serum proteins, and that, in fact, binding was increased approximately 3-fold in serum-free medium, suggesting that serum proteins may partially inhibit the binding.

TABLE 1

Processing of seven radioconjugates of Ab MA103.

| Target cell | Label | % Cpm retained by cells at (hr): | | | | $T_{1/2}$(hr) |
| --- | --- | --- | --- | --- | --- | --- |
| | | 4 | 21 | 45 | 69 | |
| SK-RC-18 | $^{125}$I | 83.0 ± 10.5 | 48.7 ± 7.6 | 28.0 ± 8.9 | 13.0 ± 2.8 | 25 |
| | DTAF-$^{125}$I | 82.6 ± 1.7 | 54.1 ± 1.1 | 38.6 ± 0.9 | 28.5 ± 0.1 | 52 |
| | DLT-$^{125}$I | 80.7 ± 3.2 | 66.3 ± 7.8 | 55.3 ± 6.5 | 48.0 ± 14.1 | 104 |
| | inulin-$^{125}$I | 71.7 ± 3.1 | 48.7 ± 2.1 | 46.3 ± 1.2 | 39.0 ± 3.0 | 151 |
| | $^{111}$In | 75.0 ± 5.3 | 58.0 ± 7.0 | 55.3 ± 6.8 | 43.0 ± 2.8 | 112 |
| SK-OV-6 | $^{125}$I | 88.3 ± 2.5 | 54.3 ± 4.7 | 35.7 ± 4.2 | 25.7 ± 2.1 | 44 |
| | B-H-$^{125}$I | 76.0 ± 4.2 | 48.5 ± 3.5 | 31.5 ± 0.7 | — | 39 |
| | fluor-gal-$^{125}$I | 88.3 ± 1.5 | 68.3 ± 4.6 | 48.7 ± 2.9 | 38.5 ± 3.5 | 58 |

Values shown are means ± standard deviations of 2–3 experiments. The $T_{1/2}$ was calculated from time points from 21–69 hr. "$^{125}$I" indicates a standard iodination with chloramine-T.

The third iodofluorescein conjugate utilized was iodo-DTAF. Iodo-DTAF labeling was considerably more efficient than any of the other non-chloramine-T iodination procedures, resulting in a specific activity of 3–5 mCi/mg (111–185 MBq/mg). Iodo-DTAF-MA103 was retained by SK-RC-18 cells slightly better than conventional $^{125}$I, but not as well as In-DTPA or DLT (Table 1). Some of the degraded material in the supernatant was precipitated by 10% TCA, and we therefore used methanol precipitation for this radiolabel. In control experiments with a conventional iodine label, TCA and methanol precipitation of culture supernatants produced indistinguishable results.

These data appear to be incompatible with results of Rushfeldt et al. above, and we therefore tested the same ligand used by these investigators, GalNAc-BSA, which was reported to enter carcinoma cells via a cell surface lectin. This protein was tested initially after a conventional chloramine-T iodination. It appeared to bind specifically and at relatively high levels to both carcinoma cells tested, SK-RC-18 and HeLa. In a well of a 96-well plate, 20–50,000 cpm were bound, of which the non-specific binding was approximately 15%. However, unexpectedly, this conventionally iodinated ligand appeared to be retained strongly by cells, with essentially no release of degraded material within 3 days. Hence, the prolonged retention of this label appeared The principle of this invention is based upon an analysis of the fate of radiolabels after degradation of the targeting protein (e.g., antibody) to which they were attached. This factor can strongly affect the dose of radiation delivered to a tumor by a targeting protein that has localized there. For example, antibody catabolism is relatively fast in comparison with the physical half-lives of the isotopes that are commonly used for radioimmunotherapy. A key aspect of this example is the selection of "typical" antibodies for the experiments, based on our evaluation of 17 antibodies reacting with 15 distinct antigens (Kyriakos et al. above; Mattes et al. above). Most previous studies of antibody internalization and processing have intentionally selected rapidly internalizing antibodies, which enter coated pits, and the results have been considered to apply only to rapidly internalizing antibodies (LaBadie et al., *Biochem. J.*, 152: 271 (1975); Geissler et al., *Cancer Res.*, 52: 2907 (1992); Anderson-Berg et al., above). Hence, a major conclusion of this work is that antibody catabolism is a critical factor not just for rapidly internalizing antibodies, but rather for all antibodies binding to the cell surface.

Table 1 provides a summary of results obtained with seven radiolabels conjugated to antibody MA103. The $T_{1/2}$, fra 1,2+ee of the rate of loss from the cell, from 21–69 hr, may provide the most meaningful measure of the retention of the label by the cell. The best residualizing labels had $T_{1/2}$'s 4-6-fold higher than conventional iodine.

Iodofluorescein conjugates were investigated, in part because of the ability of these molecules to bind to DNA. The cytotoxic potency of $^{125}I$ incorporated into DNA is well established (Warters et al. above), tetraiodofluorescein (erythrosin B) is known to bind to the nucleus of dead cells (McCoy et al., *Cancer Res.*, 36: 3339 (1976)), and diiodofluorescein is also a nuclear stain of dead cells (present results). Once molecules escape from lysosomes, they have an opportunity to enter the nucleus and bind to DNA or RNA before exiting the cell.

The DTAF label can be discussed from two perspectives. It is a fluorescein derivative, so iodinated DTAF has the potential of binding to nuclear components. However, iodo-DTAF was also reported to act as a "residualizing" label by Rushfeldt et al. above. Our experiments with iodo-DTAF have, however, indicated that iodinated GalNAc-BSA, the ligand used by Rushfeldt et al. above, binds avidly to the plastic wells, and that this is why it is not degraded. The binding of this ligand to plastic has unusual properties, such that it appears to be specific; binding was not blocked by overnight prior incubation of the wells with tissue culture medium containing 7.5% fetal bovine serum, and it was >80% blocked by excess unlabeled ligand. We suggest that this binding property might be attributed to the extensive modification of the protein; all amino groups were conjugated to glyceraldehyde, and approximately 20 carboxyl groups were conjugated to the carbohydrate hapten. This interpretation is not inconsistent with the in vivo experiments of Rushfeldt et al., above, which utilized a labeled cell suspension. In these experiments, cells were incubated for 20 hr with the ligand, so some uptake due to pinocytosis would be expected. It would not require undue experimentation to test as described above the possibility of spurious results resulting from factors such as binding of small molecules to plastic dishes.

The present results demonstrate that an effective means of destroying the viability of tumor cells consists of administering to patients a conjugate composed of a targeting protein (for example, an antibody or fragment thereof complementary to a tumor cell surface antigen, or a protein or polypeptide hormone or growth factor) covalently bound to a nucleic acid-targeting small molecule derivatized with an Auger electron-emitting radioisotope. The congugate should be able to internalize into the tumor cell and and be lytically catabolism (probably in lysosomal membranes) so as to liberate the radiolabeled small molecule. This small molecule should be capable of diffusing into the tumor cell's nucleus and binding to nucleic acids contained therein, preferably by intercalation with DNA. The decay of the radioisotope in such close proximity to the nucleic acid should decompose this molecule and decrease the viability of the tumor cell.

While the experiments discussed above have concentrated on conjugates containing a targeting antibody, other targeting proteins or polypeptides are also suitable in carrying out this invention. Such targeting proteins or polypeptides may include hormones or growth factors whose receptors are on cell surfaces and which are capable of entering the cell by, for example, receptor-mediated endocytosis.

The references cited above that provide methodology used herein are incorporated by reference.

What is claimed is:

1. A therapeutic anti-tumor conjugate, comprising a tumor cell-targeting protein or polypeptide covalently linked to a nucleic acid-targeting small molecule linked to a cytotoxically effective amount of an Auger electron-emitting radioisotope, said conjugate exhibiting the following properties:

(a) accretion of said conjugate at the surface of said tumor cell;

(b) endocytosis of said conjugate to the interior of said tumor cell;

(c) decomposition of said conjugate by an intracellular lytic enzyme located within, and endogenous to, said tumor cell, wherein said enzyme liberates from said protein or polypeptide of said conjugate said nucleic acid-targeting small molecule linked to said cytoxically effective amount of Auger election-emitting radioisotope;

(d) movement of said lytically liberated radioactive nucleic acid-targeting small molecule into the nucleus of said tumor cell;

(e) intercalation of said radioactive nucleic acid-targeting small molecule with a nucleic acid within said nucleus; and (f) extended decay of the radiolabel of said intercalating radioactive nucleic acid-targeting small molecule to emit said cytoxically effective amount of Auger electrons, wherein said decay decomposes said nucleic acid, resulting in toxicity to said tumor cell.

2. The conjugate of claim 1, wherein said Auger electron-emitting radioisotope is selected from the group consisting of $^{125}I$, $^{32}P$, $^{188}Rh$, $^{131}I$, $^{77}Br$, $^{225}At$ and $^{213}Bi$.

3. The conjugate of claim 1, wherein said nucleic acid-targeting small molecule is selected from the group consisting of a fluorescein, an acridine, a diacridine, a phenanthridine, a bis-phenanthridine, an anthracycline, a bis-anthracycline, an ethidium bromide, a mepacrine, a phenanthridium, DTAF, DLT, a methidium spermine, daunomycin, acridine orange, a diquinoline, a pyrimidone nucleoside base, and a quinazoline.

4. A method of treating a patient bearing a tumor, comprising the step of administering to said patient a therapeutic amount of said anti-tumor conjugate of claim 1 in a pharmaceutically acceptable carrier.

* * * * *